May 18, 1965 T. GREEN Plant Pat. 2,514
BOUGAINVILLEA PLANT
Filed Nov. 27, 1963
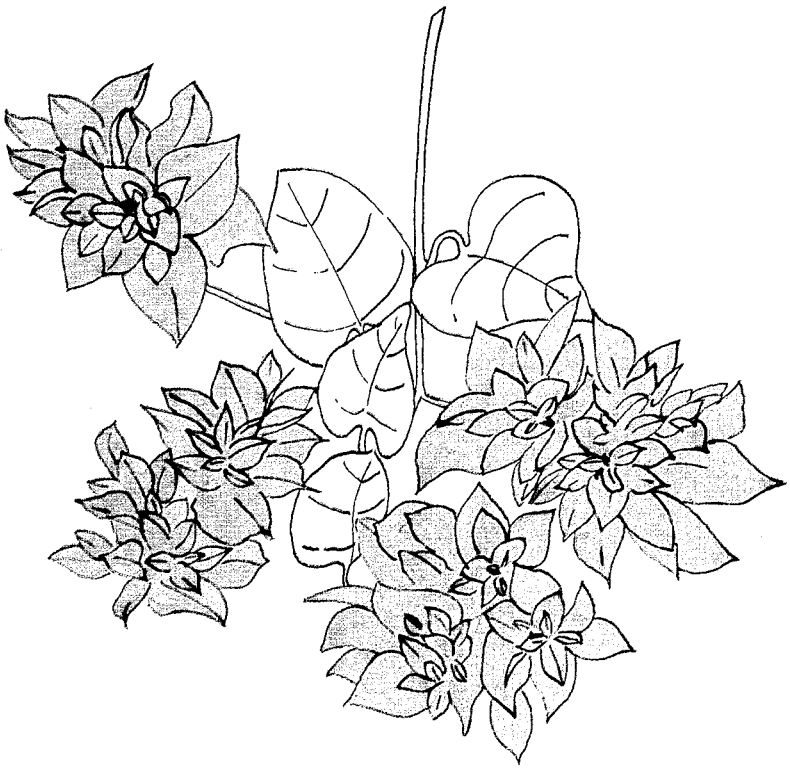
Ted Green United States Patent Office Plant Pat. 2,514
Patented May 18, 1965

2,514
BOUGAINVILLEA PLANT

Ted Green, Honolulu, Hawaii, assignor to Friends of Foster Garden, Inc., Honolulu, Hawaii Filed Nov. 27, 1963, Ser. No. 326,647
1 Claim. (Cl. Plt.—54)

The present discovery relates to a new and distinct variety of Bougainvillea plant, the original of which was a sport discovered by me in the Phillipine Islands in a cultivated area.

The original sport was a mutant branch on *Bougainvillea spectabilis* var. Crimson Lake and differs from the parent only by having multiple bracts. Basically this sport produces bracts in multiples of three, e.g., three upon three upon three, with a range up to thirty-six bracts. Each successive set arises where a flower is normally produced. There are no flowers. The size of these bracts decreases through each tripling, as one and one-half inches down to one-sixteenth inch, and gives a tufted appearance to the cluster. (See the accompanying drawing.)

This Bougainvillea's bract color can best be described as rose, or Royal Horticultural Color Chart color Rose Bengal 25/1.

I have now one hundred of these plants which were asexual reproductions made by cuttings and air-layering. All propagants demonstate the same character as the original sport.

I claim:

A new and distinct variety of Bougainvillea plant, characterized as to novelty by the tripling of the bracts, substantially as shown and described.

No references cited.

ABRAHAM G. STONE, *Primary Examiner.*